Figure 1:
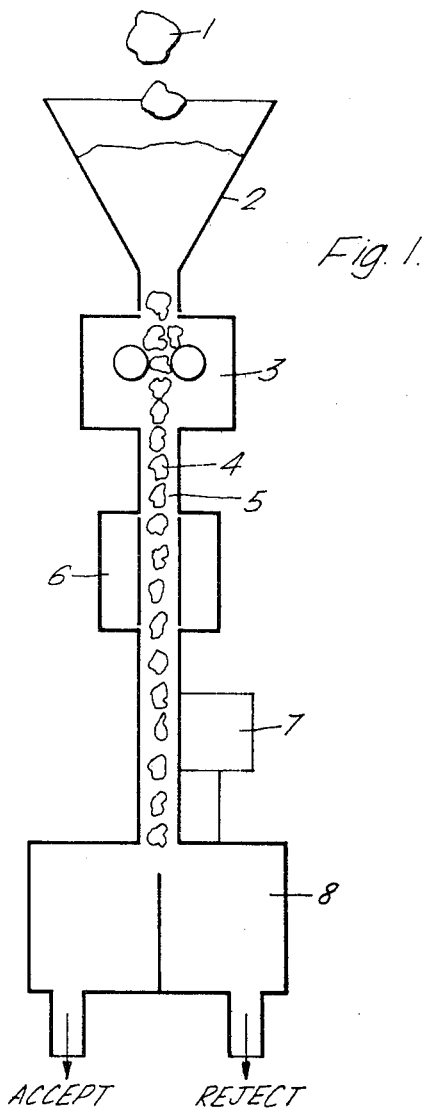

United States Patent [19]
Clayton et al.

[11] 4,340,443
[45] Jul. 20, 1982

[54] ANALYSIS OF GOLD-CONTAINING MATERIALS

[75] Inventors: Colin G. Clayton; Malcolm R. Wormald, both of Abingdon, England

[73] Assignee: United Kingdom Atomic Energy Authority, London, England

[21] Appl. No.: 157,300

[22] Filed: Jun. 9, 1980

[30] Foreign Application Priority Data

Jun. 14, 1979 [GB] United Kingdom ............. 7920667

[51] Int. Cl.³ .............................................. G21G 1/06
[52] U.S. Cl. .................................................. 376/342
[58] Field of Search ................. 176/10; 250/302, 303, 250/253, 255

[56] References Cited

U.S. PATENT DOCUMENTS 3,052,353 9/1962 Pritchett ............................. 250/303
4,171,485 10/1979 Marshall ............................. 250/255

OTHER PUBLICATIONS

J. of Radioanalytical Chem., vol. 33, 1976, pp. 243-249.
J. of Radioanalytical Chem., vol. 31, 1976, pp. 365-375.

Primary Examiner—Harvey E. Behrend
Attorney, Agent, or Firm—William R. Hinds

[57] ABSTRACT

A method for determining the gold content of an auriferous material, comprising the operations of irradiating a body of the material with neutrons and determining the intensity of $\gamma$-rays having an energy of 279 keV arising from the reaction $^{197}$Au (nn') $^{197m}$Au→279 keV. Apparatus for carrying out the method also is described.

8 Claims, 2 Drawing Figures

ANALYSIS OF GOLD-CONTAINING MATERIALS

The present invention relates to the determination of the gold content of auriferous materials, and in particular to the determination of the gold content of auriferous rock samples.

Gold may occur at depth in thin bands of mineralisation which when mined together are accompanied by substantial quantities of barren rock. In order to prevent the expensive and time consuming treatment of all mined material, it is necessary that some pre-selection process be applied to the mined material. A number of methods of selecting rocks for processing have been proposed but to date no entirely satisfactory method of selection has been found.

Some methods have failed because they are secondary methods and the correlation between the secondary property measured and the gold content is either variable or inaccurate; other have not been able to cope with the throughput of samples necessary in a production environment.

The present invention provides a method of determining the gold content of mined rock which is both capable of coping with the required throughput of rock samples, and utilises a property of the gold itself to determine its concentration in the rock samples.

According to the present invention there is provided a method for determining the gold content of an auriferous material, comprising the operations of irradiating a body of the material with neutrons and determining the intensity of γ-rays having an energy of 279 keV arising from the reaction $^{197}$Au (nn') $^{197m}$Au→279 keV.

If the method is being used for the determination of the gold content of auriferous rock, then it is necessary to use a neutron source which does not produce neutrons which have an energy above the neutron reaction thresholds of elements such as Al, Si, Ca, Fe and O which are likely to be present in high concentrations. For example, suitable neutron sources are tube sources which utilise the deuteron-deuteron or deuteron-beryllium reaction to produce neutrons.

Figure 2:
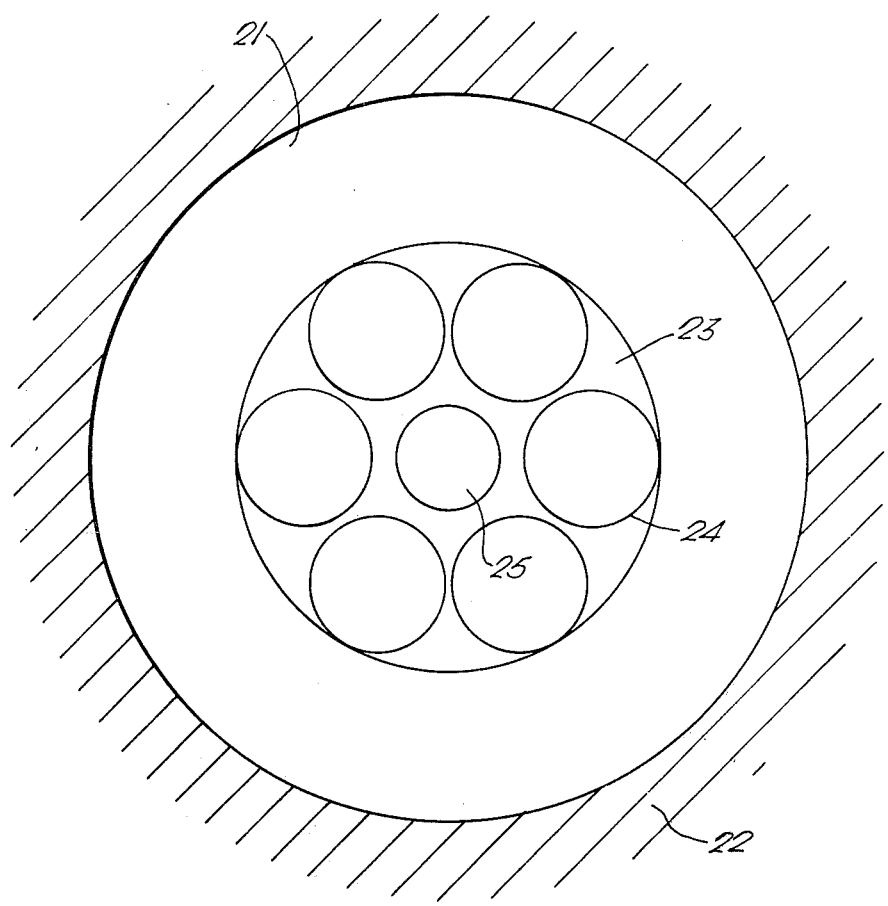

The invention will now be described, by way of example, with reference to the accompanying drawings in which, FIG. 1 is a schematic diagram of a rock-sorting apparatus embodying the invention, and FIG. 2 is a diagrammatic cross-section of a neutron radiation assembly for use in the apparatus of FIG. 1.

Referring to the drawings, auriferous rock 1 is fed to a hopper 2 which supplies it to a rock crusher 3 in which it is crushed into lumps 4 corresponding to a mesh size of some 5 cm. The stream of crushed rock leaving the crusher 3 is divided into a number of streams 5 only one of which is shown, which pass through a neutron irradiation assembly 6, to be described more fully later. Having been irradiated by neutrons generated within the assembly 6, each of the streams of lumps 4 of rock is caused to pass a γ-ray detector assembly 7 which is arranged to detect any γ-rays having an energy of 279 keV arising from the nuclear reaction $^{197}$Au (nn') $^{197m}$Au, occurring in any gold contained in the lumps 4 of rock. Each lump 4 of rock is interrogated individually to establish whether its gold content lies above or below some predetermined concentration. For example, the critical concentration might be 5 ppm. In general it might be in the range 1 to 10 ppm.

Downstream of the γ-ray detector assembly 7 is a sorter 8 of a type which is well known in the art of material sorting, and which will not be described further. The sorter 8 is arranged to respond to signals from the γ-ray detector assembly 7 to accept or reject for further processing each lump 4 of rock passing through it.

Referring to FIG. 2, the neutron irradiation assembly 6 consists of a cylindrical body 21 made of lead which is surrounded by a biological radiation shield 22 which is made to be impervious to neutrons and to γ-rays. In the body 21 there is a central bore 23 around the periphery of which there are positioned six tubes 24 made of boron. The tubes 24 extend throughout the length of the body 21. Each of the tubes 24 has a bore which is such that only a single stream of lumps 4 of rock can pass through the relevant tube. In the central region of the bore 23 in the body 21 there is a target 25 made of a material which will produce neutrons in response to bombardment by a beam of deuterons from a source which is not shown. Suitably, the target 25 can be made of a material which contains deuterons, or beryllium. The important thing is that the neutron source should be made of a material which does not produce neutrons which are energetic enough to excite fast neutron reactions in the constituent elements of the rock in which the gold is contained, i.e. aluminum, silicon, calcium, iron and oxygen. The target 25 will emit neutrons over a solid angle of 4Π, but as the lumps 4 of rock pass through the maximum neutron field at 90° to the direction of the neutrons, it can be arranged that while the neutron source energy equates to the maximum energy of the reaction $$^{197}Au(nn')^{197m}Au,$$

the neutron energy is below the threshold energies of (n,p) reactions in such as those previously mentioned which are likely to be present in the rock in high concentrations. In particular care should be taken to ensure that the neutron energy is below the threshold of the fluorine reaction $$^{19}F(n,\alpha)^{16}N_\beta \rightarrow ^{16}O(T_{\frac{1}{2}}=7.3 \text{ secs})$$

This reaction generates γ-rays having energies of 6.1 and 7.2 Mev. Although these are considerably greater than the 0.279 Mev from the $^{197m}$Au, the half-life is the same, and the reaction could be the source of low-energy collided γ-rays which would have the same decay pattern as those to be detected, and so interfere with the estimation of the gold content of the lumps 4 of rock, particularly if the fluorine is present in concentrations which are relatively high when compared to that of the gold.

The γ-ray detector assembly 7, which is not illustrated in detail, has six linear arrays of γ-ray detectors, one for each stream of lumps of rock. The signals which operate the sorter 8, which again has six input channels, are derived from the combined output signals from each of the individual γ-ray detectors appropriate to each channel.

A neutron output of some $10^{11}$ n/s from the neutron source enables a lump of rock having a gold concentration of 1 ppm to be differentiated from one having a gold concentration of 2 ppm in one of three measurements, and a lump having a gold concentration of 2 ppm to be differentiated from one having a gold concentration of 5 ppm in 99 in 100 measurements.

We claim:

1. A method for determining the gold content of an auriferous material, comprising the operations of irradiating a body of the material with neutrons and determining the intensity of γ-rays having an energy of 279 keV arising from the reaction $^{197}$Au (nn′) $^{197m}$Au→279 keV.

2. A method according to claim 1, wherein there is used a neutron source which does not produce neutrons which have an energy sufficient to excite fast neutron reactions in non-auriferous constituents of the auriferous material.

3. A method according to claim 2, wherein there is used a neutron source which produces neutrons by means of the deuteron-deuteron or deuteron-beryllium reaction.

4. Apparatus for determining the gold content of an auriferous material, comprising means for passing discrete samples of auriferous material past a source of neutrons, and means for determining the intensity of γ-rays having an energy of 279 keV arising from the reaction $^{197}$Au (nn′) $^{197m}$Au→279 keV.

5. Apparatus according to claim 4, wherein there is included means responsive to the means for determining the intensity of γ-rays arising from the reaction $^{197}$Au (nn′) $^{197m}$Au →279 keV to separate those samples of auriferous material having a gold content above a predetermined value from those which do not.

6. Apparatus according to claim 4, wherein the neutrons are provided by a tube source utilising the deuteron-deuteron or deuteron-beryllium reaction to generate the neutrons.

7. Apparatus according to claim 4, wherein the means for passing discrete sources of auriferous materials past a source of neutrons comprises a plurality of tubes regularly disposed parallel to one another around the periphery of a central tube adapted to contain a source of neutrons having energies which are insufficient to excite fast neutron reactions in non-auriferous constituents of the samples of auriferous material, and means for directing the samples of auriferous material into the said tubes.

8. Apparatus according to claim 7, wherein there is a separate γ-ray detector channel and responsive sorter associated with each of the said tubes.

* * * * *